(12) United States Patent
O'Shea et al.

(10) Patent No.: US 6,312,738 B1
(45) Date of Patent: Nov. 6, 2001

(54) AZADIRACHTIN EXTRACTION PROCESS

(75) Inventors: Michael J. O'Shea; Donald J. Brushett; David J. Pollard, all of New South Wales (AU)

(73) Assignee: Neem Extracts Pty. Ltd., Holland Park (AU)

( * ) Notice: Subject to any disclaimer, the term of this patent is extended or adjusted under 35 U.S.C. 154(b) by 0 days.

(21) Appl. No.: 09/462,598

(22) PCT Filed: Jul. 13, 1998

(86) PCT No.: PCT/AU98/00542

§ 371 Date: Jan. 14, 2000

§ 102(e) Date: Jan. 14, 2000

(87) PCT Pub. No.: WO99/02533

PCT Pub. Date: Jan. 21, 1999

(30) Foreign Application Priority Data

Jul. 11, 1997 (AU) .................................................. PO7861

(51) Int. Cl.[7] .......................... A61K 35/78; A61K 31/35; A01N 25/00; C07D 313/00
(52) U.S. Cl. .......................... 424/761; 424/405; 514/453; 549/354
(58) Field of Search ................................. 424/195.1, 405, 424/761; 514/453; 549/354

(56) References Cited

U.S. PATENT DOCUMENTS

| H1541 | * | 6/1996 | Holla | 424/195.1 |
|---|---|---|---|---|
| 4,943,434 | * | 7/1990 | Lidert | 424/195.1 |
| 5,281,618 | | 1/1994 | Walter | 424/195.1 |
| 5,391,779 | | 2/1995 | Lidert | 514/453 |
| 5,395,951 | * | 3/1995 | Nagasampagi et al. | 549/383 |
| 5,695,763 | * | 12/1997 | Kleeberg | 424/195.1 |

FOREIGN PATENT DOCUMENTS

| 0 311 284 | | 4/1989 | (EP) . |
|---|---|---|---|
| 0 405 291 | | 1/1991 | (EP) . |
| 99/025133 | * | 1/1999 | (WO) . |

OTHER PUBLICATIONS

Feuerhake, "Development of a standardized and formulated insecticide from a crude neem kernel extract", *Z. Pfanzenkrankh. Pflanzenschutz*, (1985), 92(6), pp. 643–649.

Feuerhake, "Effectiveness and Selectivity of Technical Solvents for the Extraction of NEEM Seed Components with Insecticidal Activity", *Schriftenr. GTZ*, 1984), 161 (*Nat. Pestic. Neem Tree Other Top. Plants*), pp. 103–113.

* cited by examiner

*Primary Examiner*—Christopher R. Tate
(74) *Attorney, Agent, or Firm*—Nixon & Vanderhye (57) ABSTRACT

A process of producing an azadirachtin-rich aqueous solution is disclosed which comprises de-oiling by pressing whole or ground neem seeds to remove a first proportion of the oil content; extracting the de-oiled neem seeds with a polar organic solvent in which the azadirachtin is soluble but in which polysaccharides and proteins are not substantially soluble; partitioning the organic solvent solution against water to form an aqueous solution of azadirachtin and the remaining oil; and separating the remaining oil from the azadirachtin-rich aqueous solution. Additional steps of the process are also disclosed.

24 Claims, 6 Drawing Sheets

AZADIRACHTIN EXTRACTION PROCESS

FIELD OF THE INVENTION

The present invention relates to a process for the recovery of azadirachtijn and/or similar insecticidal compounds from neem seeds.

BACKGROUND ART

It is known that the seeds and other parts of the neem tree (*Azaderachta indicia* and related species) contain natural pesticidal compositions. The main active pesticidal composition is azadirachtin which is a tetraniortriterpenoid that causes feeding inhibition and growth inhibition in a variety of organisms including insects, mites and neniatodes. It is possible that there are a number of similar insecticidal compounds present in neem extracts that partition with the azadirachtini. As used in this specification, the term azadirachtin is taken to include all insecticidal terpenoids present in neen extracts that partition with azadirachtin.

In recovering azadirachtin from neem seeds it is necessary to separate the active constituent from other materials including the other triterpenes, the oil. fibre and other insoluble materials. and water soluble constituents such as sugars and water soluble proteins. These separation procedures are complicated by the fact that azadirachtin is susceptible to hydrolysis in water and to heat degradation.

One conventional method for extracting azadirachtin from neem seeds involves the use of three organic solvents and two liquid/liquid partition steps. Firstly, the neem seeds are pressed to remove the majority of the neem oil. The resulting expeller cake is then extracted with methanol. The methanol extracts a wide range of substances including azadirachtin and the other triterpenies, diterpenies, the residual oil, and some polysaccharides and proteins. To produce a powder from the methanolic supernatant, the extract must undergo a number of clean-up steps.

In the first clean-up step, the supernatant is concentrated and partitioned against hexane, or a similar non-polar solvent, to remove the oils and diterpenes. The hexane is then driven off in a still and the resulting oil is collected. The second clean-up step involves taking the de-oiled supernatant and driving off the methanol. The resulting tar is then resolved in ethyl acetate, or a similar solvent, and partitioned against water to remove the polysaccharides and water soluble proteins. The ethyl acetate which contains the azadirachtin and other triterpenes is then evaporated to produce an azadirachtin rich powder.

There are a number of problems associated with this conventional method, with the major problem being cross-contamination of the solvents used in the process and the resulting variation in product quality. While good quality azadirachtin powder can be produced when first using the process with fresh solvents. after a number of cycles problems with cross-contamination do arise. While hexane and methanol are normally considered essentially immiscible, in a multi-component system, such as is created during the extraction of azadirachtin described above, the hexane and methanol do demonstrate some miscibility. The change in the polarity of the solvents allows oils to be carried through the hexane partition and so creates difficulties in producing a non-oily or flowable powder. A more serious problem is any occurrence of cross-contamination between the methanol and ethyl acetate. If the methanol is not removed in the drying step after the hexane partition, cross-contamination with ethyl acetate occurs. This contamination of the ethyl acetate with methanol causes azadirachtin to be carried over into the water in the ethyl acetate/water partition or in the worst case prevents a partition forming at all.

A further problem with the conventional method for extracting azadirachtin is the production of waste water with a high biological oxygen demand (BOD). In many countries, the release of waste water with high BOD is not permitted and requires the installation of a relatively expensive water treatment facility.

An alternative azadirachtin extraction process is described in Australian patent no 661482 to Trifolio-M GmbH, Herstellung Und Vertrieb Hochreinier Biosubstanzen. In this alternative process, the neem seed is pressed or crushed to remove the majority of the oil and the expeller cake is extracted with warm water. The warm water extraction removes the azadirachtin, some of the more polar triterpenes, the majority of the polysaccharides and water soluble proteins, and a slight amount of the more polar oily compounds. The aqueous supernatant is partitioned against a solvent of intermediate polarity, such as ethyl acetate or dichloromethane. with the azadirachtin partitioning into the organic layer. The organic layer can then be concentrated under vacuum and the azadirachtin precipitated through the addition of a nioni-polar solvent, such as hexanie or petroleum ether. While high yields of azadirachtin powder are produced using this alternative process, the process still results in the discharge of an aqueous solution loaded with polysaccharides and proteins which, in some countries, will require treatment to meet environmental standards. Further, the precipitation step where a non-polar solvent is added to the concentrated supernatant results in cross-contamination with its attendant problems and expense of requiring purification of the solvents prior to their re-use in the extraction process.

SUMMARY OF THE INVENTION

According to a first aspect, the present invention consists in a process for the production of all azadirachtin rich aqueous solution comprising the steps of:

(i) de-oiling ground or otherwise comminuted neem seeds to remove a first proportion of the oil content thereof;

(ii) extracting the de-oiled neem seeds with a polar organic solvent, in which azadirachtin is soluble but in which polysaccharides and proteins are not substantially soluble, to form an organic solution of azadirachtin and the remaining oil;

(iii) partitioning the organic solution against water to form an aqueous solution of azadirachtin and the remaining oil; and (iv) separating the remaining oil from the aqueous solution to form an azadirachtini rich aqueous solution.

In one embodiment, the process can further comprise the steps of:

(v) extracting the aqueous solution with a polar organic solvent, in which azadirachtin is soluble but in which polysaccharides and proteins are not substantially soluble, to form an organic solution of azadirachtin; and (vi) evaporating the organic solvent to form an azadirachtin rich powder.

The neem seeds are preferably first dried to a moisture content of from 1 to 10% by weight, more preferably 2 to 4% by weight, and then pressed to produce an expeller cake of seeds from which has been removed a substantial proportion of the oil content of the seeds. Preferably, the pressing is done at a low speed to reduce the temperature build up in the neem seeds during pressing and so minimise heat degradation of the azadirachtin. The pressing is. however, preferably conducted so that at least 70% by weight, more preferably 80% by weight, and most preferably 90% by weight of the oil is removed from the seeds during the pressing process.

The polar organic solvent used to extract the substantially de-oiled expeller cake in step (ii) is preferably selected from the following: ethyl acetate. methyl acrylate, butanol, 2-butanone, butyl carbitol, ethylene glycol monio bhityl ether, ethyl formate, propyl formate, furan, tetrahydiroftuiran. isopherone, 2,4-dihydroxy 4-methyl pentanone, 2,4-dimethyl pentanone, dibutyl phthalate, dipentyl phthalate, 1,2-epoxy propane. dibutyl sebacate, chloroform, dimethyl sulphide, ethanthiol, ethyl chloride. pentachloroethane, trichloroethene, 1-bromopentane or another solvent with a similar dielectric constant and mixtures thereof.

Ethyl acetate is preferred and can be used in the process as it is not polar enough to extract the polysaccharides and proteins from the expeller cake but is sufficiently polar to extract the azadirachtin, the other triterpenes, and any residual oil from the expeller cake. The ratio of expeller cake to ethyl acetate in the extraction can be 1:1. The extraction produces an ethyl acetate supernatant of azadirachtini and oil with the majority of the polysaccharides and proteins, which are not soluble in the ethyl acetate, remaining in the expeller cake. This step in the process is particularly advantageous as it significantly reduces the biological oxygen demand (BOD) of any waste solutions produced later by the process and so removes the need for expensive waste water treatment processes as is required by the conventional azadirachtin extraction process. While other solvents can be employed in the extraction step as defined above. The remainder of the specification will be directed to a process using ethyl acetate at step (ii). Modifications to the process as defined below when using different solvents would be readily envisaged by a person or ordinary skill in the art of solvent extraction.

The ethyl acetate supernatant can be concentrated by distillation under vacuum prior to step (iii). For example, about half of the ethyl acetate can be removed from the supernatant during the distillation. If desired, the supernatant could be filtered at this time through a filter press or bag filters. Such filtering would serve to help prevent the formation of a colloidal layer in the following partition. The concentrated supernatant can then undergo step (iii) defined above. The water is preferably warm, having a temperature between about 20° C. and 40° C. In this partition, the azadirachtin. Most of any other highly polar triterpenies present in the supernatant, and the polar fractions of the remaining oil transfer into the aqueous layer along with a proportion of the ethyl acetate. The organic layer produced by the partition preferably contains a minimal amount of azadirachtin but is preferably rich in the less polar triterpenes and diterpenes or "bitters" as they are known in the art. The organic layer call be distilled under vacuum and the ethyl acetate recovered leaving a "bitter" oil that also contains many biologically active compounds.

The aqueous solution formed by the partition with the water can be cooled prior to the oil separation step (step (iv)). The oil is preferably separated from the water on the basis of the different densities of the oil and water. The separation call be undertaken by passing the aqueous solution through a separator where the solution is spun through a series of cones that physically separate the oil and water on the basis of their densities. The oil stream which preferably contains no azadirachtin but does contain the less polar triterpenes and the diterpenes can be combined with the organic layer from the water partition and distilled as described above.

In step (v), the azadirachtin-rich aqueous solution, which also still contains most of any other highly polar triterpenes and any remaining polysaccharides and proteins not left in the expeller cake by the ethyl acetate extraction, is preferably extracted with ethyl acetate. While ethyl acetate is preferred, extraction could also be undertaken using methyl acrylate, butaniol, 2-butanonie, butyl carbitol, ethylene glycol mono butyl ether, ethyl formate, propyl formate, furan, tetrahydrofurani isoplieronle. 2.4-dihydroxy 4-methyl pentanionie, 2,4-dimethyl pentanione, dibutyl phthalate, dipentyl phthalate, 1,2-epoxy propane, dibutyl sebacate, chloroforin, toluene, benzene. dimethyl sulphide, ethanlthiol, ethyl chloride, pentachloroethanie, trichloroetheine, 1-bromopentanie or another solvent with a similar dielectric constant. While other solvents can be employed in step (v), the remainder of the specification will be directed to a process wherein ethyl acetate has been used as defined above in step (v). A person or ordinary skill in the art could readily envisage the modifications required to the defined process if a listed alternative solvent was used in step (v).

On extraction with ethyl acetate, the azadirachtini and other highly polar triterpenes partition completely into the ethyl acetate layer. The resulting aqueous layer which contains the remaining polysaccharides and proteins, which are not soluble in the ethyl acetate, can go to waste or be utilised in other processes. The level of polysaccharides and proteins in the aqueous layer is preferably sufficiently low to allow the waste water to be disposed without the need for significant and expensive treatment.

In one embodiment, the aqueous solution prior to step (v) can be salted to ensure all of the azadirachtini is removed from the aqueous phase in this step. In another embodiment, the solubility of the azadirachtin in the aqueous solution is reduced by lowering the temperature of the aqueous solution. The present inventors have found that the solubility of azadirachtini in water is reduced in water having a temperature of 10° C. or less. By appropriately lowering the temperature of the aqueous phase, the quantity of azadirachtin in the organic phase can be increased.

At step (vi), the organic layer is preferably passed through a scrape side rotary evaporator which evaporates the ethyl acetate leaving the azadirachtini rich powder. The evaporated ethyl acetate, which has not been contaminated with other organic solvents during the process, can be condensed and recycled ready for immediate use in step (ii) of the extraction process.

The process can in another embodiment further include the step of resolving the azadirachtini powder in methanol in a vessel. In methanol. only the triterpenes are soluble and any oils still remaining after step (iv) attach to the side of the vessel and are so separated from the azadirachtiln rich methanol solution. The methanol can then be evaporated to produce an even less oily azadirachtini rich powder.

In a still further embodiment, the process can include a filtering step prior to step (vi). The filtering step preferably comprises passing the azadirachtin rich supernatant through a hydrophobic filter medium. Any oils remaining in the supernatant preferably bind to the hydrophobic medium.

According to a second aspect, the present invention consists in a process for the production of an azadirachtini rich aqueous solution comprising the steps of:

(a) partitioning an organic solution of azadirachtin against water to form an aqueous solution of azadirachtin., the organic solution being formed by the extraction of substantially de-oiled neem seeds with a polar organic solvent, in which azadirachtin is soluble but in which polysaccharides and proteins are not substantially soluble; and (b) separating any remaining oil front the aqueous solution to form the azadirachtini rich aqueous solution.

In this aspect, the extraction of the substantially de-oiled neem seeds with the polar organic solvent can be performed on or near the site of the neem seed collection. The oily ethyl acetate solution. Which can also be distilled on site, can then be shipped to a processing facility where steps (a) and (b) can be performed. There are a number of advantages in splitting the process, including:

the quality of the azadirachtini and neem oil is best when the seed is pressed while it is fresh just after picking; and the shipping costs are reduced as the azadirachtin concentration in the seeds is about 0.35–0.40% whereas the concentration is about 2–3% in the concentrated organic solution.

The described embodiments of the first aspect of the invention are equally applicable to the second aspect. With steps (a) and (b) being considered equivalent to steps (iii) and (iv) of the process defined in the first aspect of the invention.

According to a still further aspect, the present invention comprises an azadirachtin rich solution produced according to the processes defined herein.

According to yet a further aspect, the present invention comprises an azadirachtin rich powder produced according to the processes defined herein.

The powder preferably comprises at least about 45% by weight of azadirachtin.

BRIEF DESCRIPTION OF THE DRAWINGS

By way of example only, a preferred embodiment of the invention is now described with reference to the accompanying drawings, in which.

PREFERRED MODE OF CARRYING OUT THE INVENTION

Figure 1:
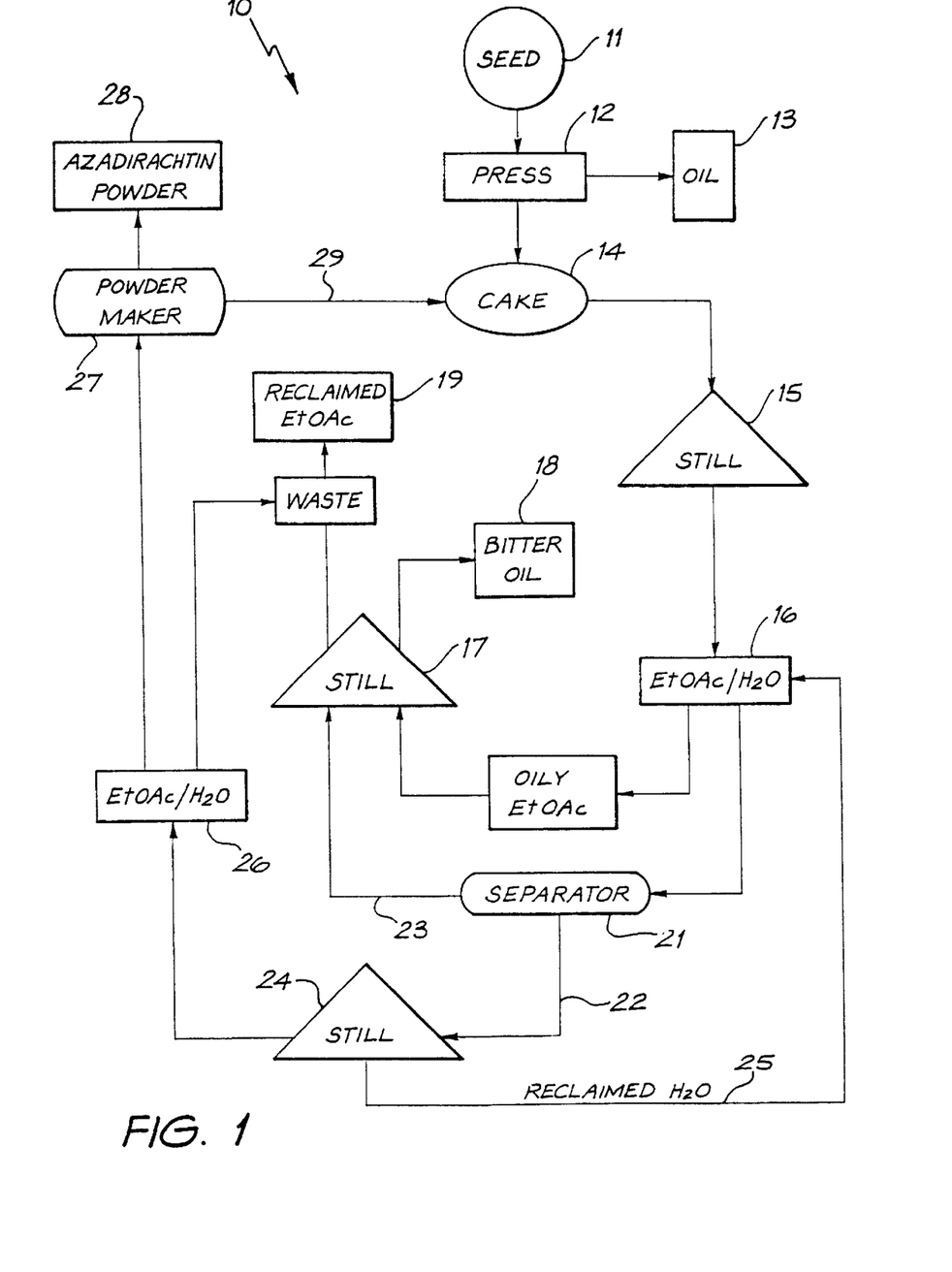
FIG. 1 is a schematic diagram of one embodiment of the azadirachtin extraction process according to the present invention.

A process for producing azadirachtin powder from neem seeds is depicted generally as 10 in FIG. 1.

Seeds 11 from a neem tree are collected and dried to a moisture content of about 2–3% by weight, finely ground and passed through a press 12 to remove about 90% by weight of the oil content thereof. The oil is then passed through a filter press and dewaxed through filtering or cooling to produce a clean neem oil 13. The pressing of the neem seeds 11 can be undertaken at or near the site of harvest of the neem seeds 11.

Figure 2:
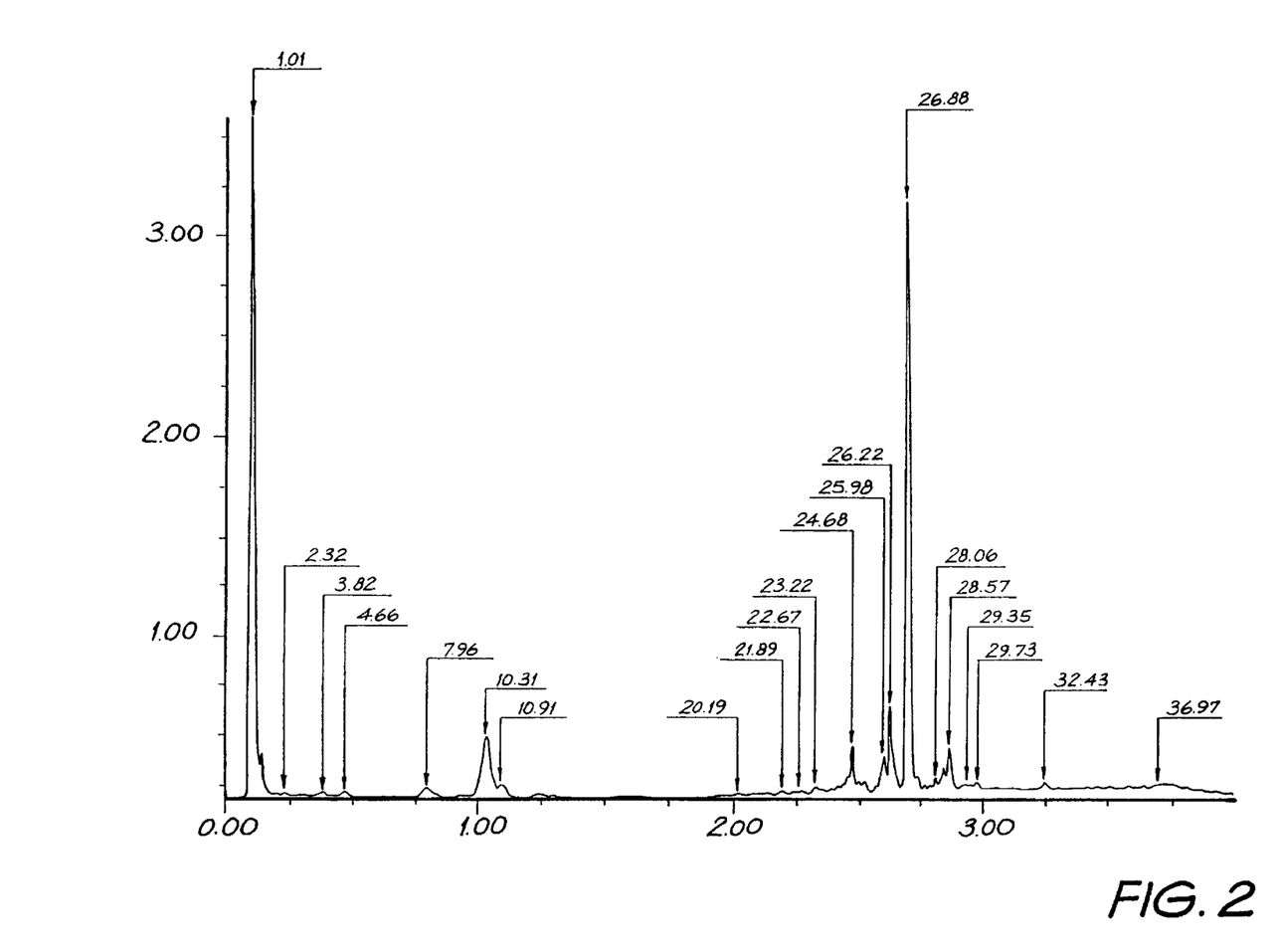
FIG. 2 is a chromatogram of a methanolic extract produced in a prior art azadirachtin extraction process from neem seeds.
Figure 3:
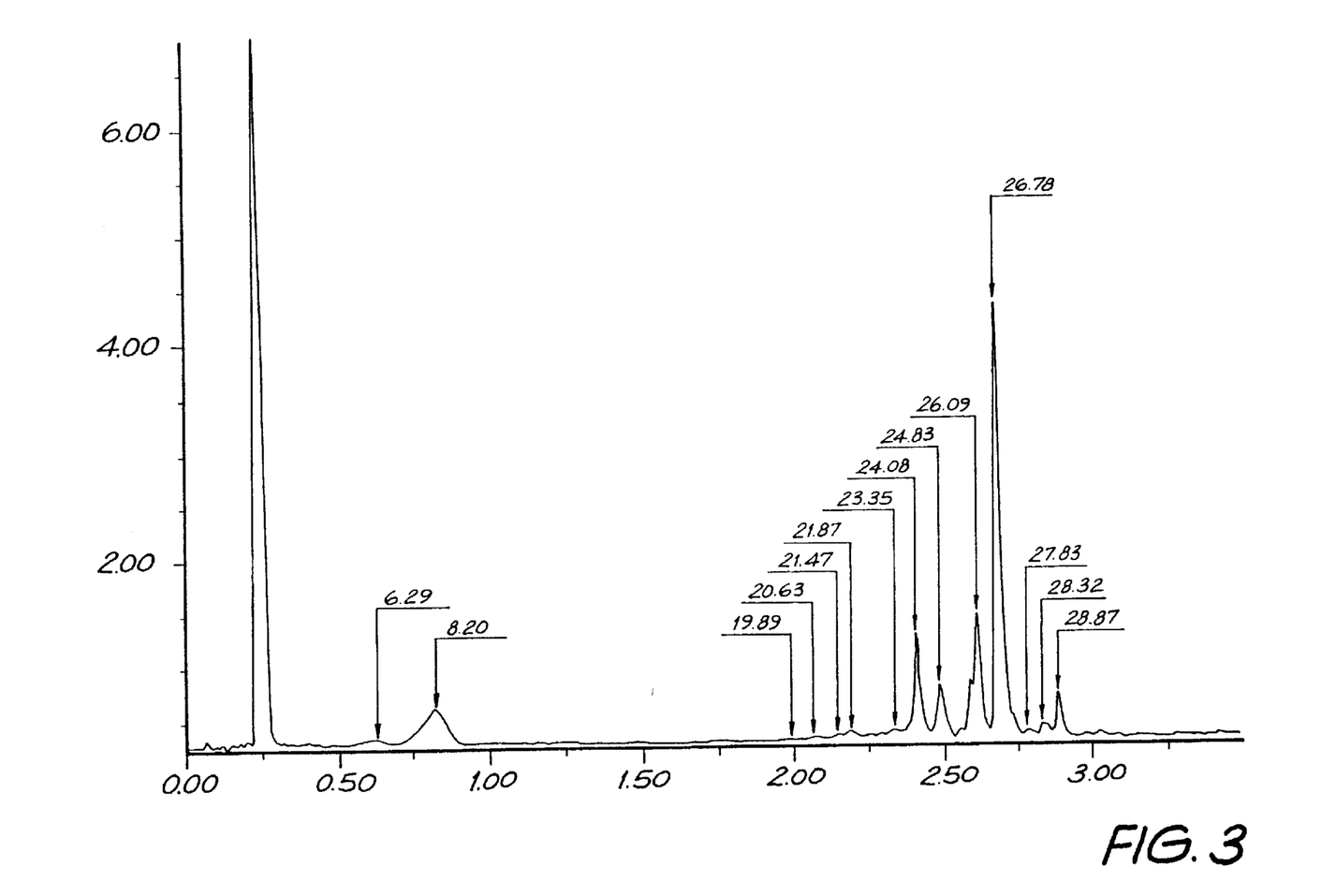
FIG. 3 is a chromatogram of the ethyl acetate extract of neem seeds produced by the process depicted in FIG. 1.

The resultant expeller cake 14 produced by the press 12 is extracted with ethyl acetate at a ratio of about 1:1 in a counter current extraction unit. Once again, if desired, this extraction step can be undertaken at or near the site of harvest of the neem seeds 11. The majority of the polysaccharides and proteins which are not soluble in the ethyl acetate remain in the expeller cake following the extraction. The azadirachtini along with the other triterpenes, diterpenes and the remaining oil partition into the ethyl acetate solution. A chromatogram of the ethyl acetate extract is attached as FIG. 3. For comparison. FIG. 2 is a chromatogram of a methanolic extract of neem seeds produced in a conventional process. In the conventional process, the methanolic extract contains polysaccharides and proteins (the large first peak on the chromatogram), azadirachtin (retention time≈10 min.), other triterpenes (retention time 20–30 min.) and a small amount of oily compounds (retention time>30 min.). The chromatogram at FIG. 3 reveals that the ethyl acetate extract contains very little polysaccharides and proteins compared to the mnethanolic extract, with azadirachtin present as well as the other triterpenes and some oily compounds.

Figure 4:
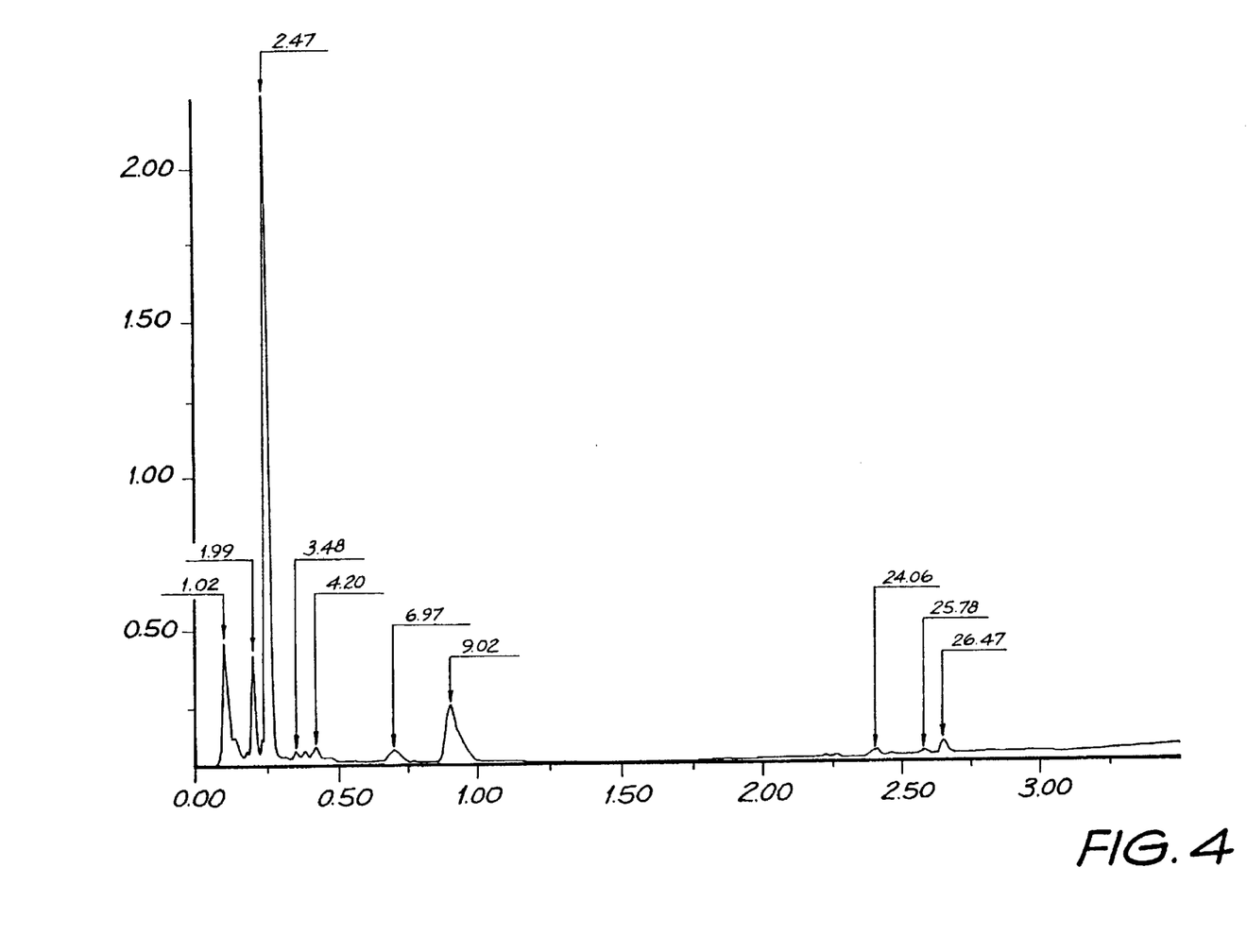
FIG. 4 is a chromatogram of the water fraction following partition of the ethyl acetate supernatant with water in the process depicted in FIG. 1.
Figure 5:
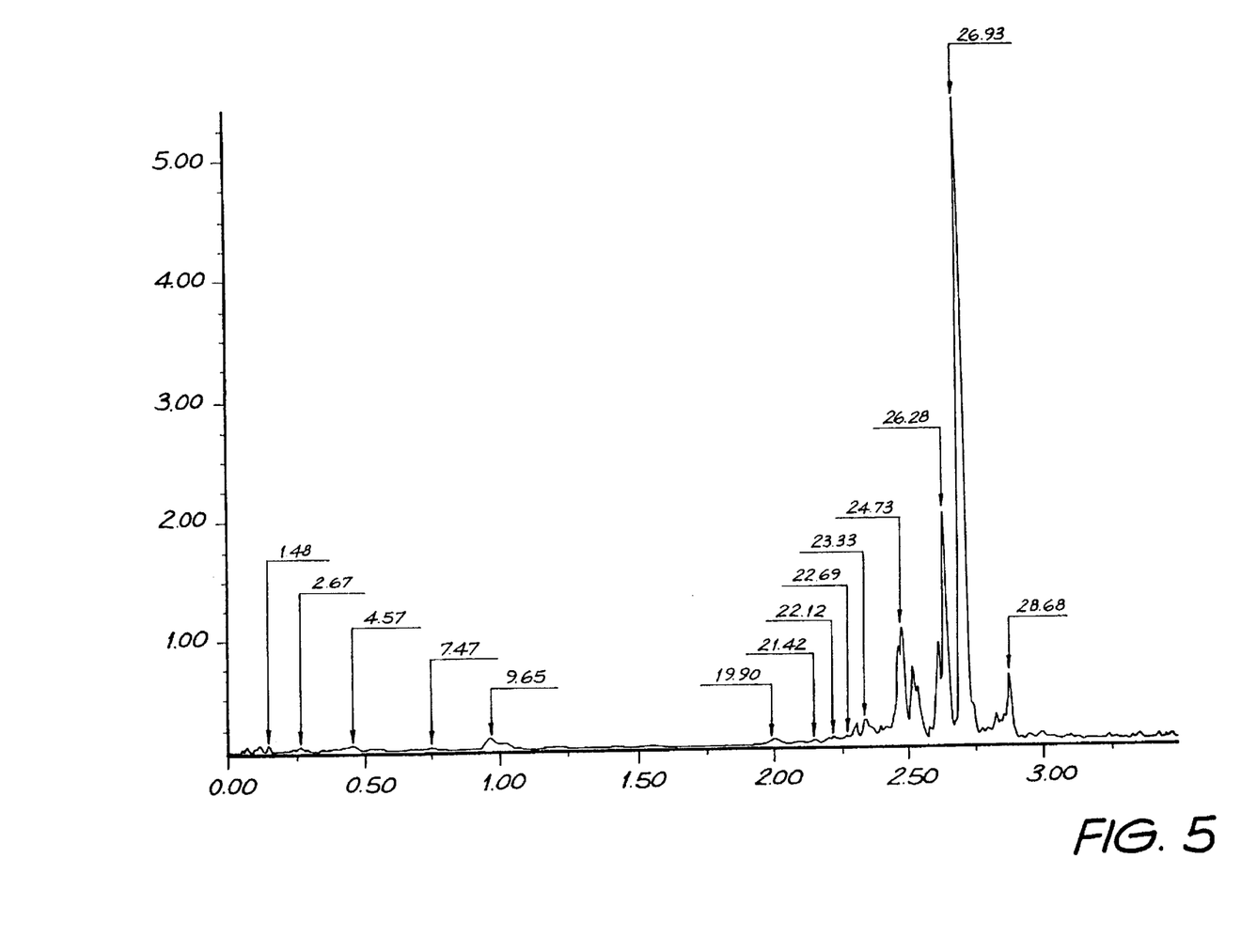
FIG. 5 is a chromatogram of the oily ethyl acetate fraction following partition of the ethyl acetate supernatant with water in the process depicted in FIG. 1.

The ethyl acetate supernatant is then concentrated under vacuum in a still 15 with a proportion (eg: about half) of the ethyl acetate being removed from the supernatant. The concentration of the supernatant is monitored by a determination of the viscosity of the supernatant. This step can also be undertaken at or near the site of harvest of the neem seeds 11. The concentrated supernatant is then partitioned against warm water (about 20–40° C.) (step 16). In this partition, the azadirachtin. Most of the other triterpenes, and the more polar fractions of the remaining oil transfer into the aqueous layer along with an amount of ethyl acetate. The chromatogram of the water fraction, attached as FIG. 4, confirms that the azadirachtin transfers almost completely to the water fraction of the partition (the large peak at the front of the chromatogram in FIG. 4 is an ethyl acetate peak). The chromatogram of the ethyl acetate fraction attached as FIG. 5 confirms that very little azadirachtin is carried over with the oily ethyl acetate but that the vast majority of the other triterpenes remain mostly in this fraction. The dynamics of this partition are intricate as the azadirachtin exhibits a higher solubility in water in the presence of ethyl acetate than without. The partition becomes a complex multi-component system, and even some of the compounds that have little solubility in water are carried across into the aqueous layer by the ethyl acetate. The organic layer contains a minimal amount of azadirachtin but is rich in the less polar triterpenes and diterpenes ("bitters"). The organic layer is passed to a still 17 to allow recovery of the ethyl acetate leaving a "bitter" oil 18 which contains many biologically active compounds. The recovered ethyl acetate 19 can be recycled ready for re-use to extract the expeller cake 14.

The aqueous layer produced by the warm water partition contains enough oily compounds to prevent the formation of a flowable powder directly. On cooling, a visible change takes place in the supernatant with small oil droplets seen to form. At this point a physical separation of the oil and water is possible. The aqueous supernatant is run through an oil separator 21 where the solution is spun through a series of cones (at speeds preferably about or in excess of 3500 rpm) which physically separates the oil and water on the basis of their different densities. The water stream 22 from the separator 21 contains azadirachtin and some of the more polar triterpenes. The oil stream 23 basically contains no azadirachtin but does contain the less polar triterpenes and diterpenes and oily compounds. As depicted in FIG. 1, the oil stream 23 is combined with the organic layer from the warm water partition and distilled under vacuum in still 17 as described above.

The water stream 22 is concentrated under vacuum in a still 24 until a proportion (eg: about 75%) of the water is removed from the stream. The evaporated water 25 is recondensed and recycled ready for use in the warm water partition 16 described above.

Figure 6:
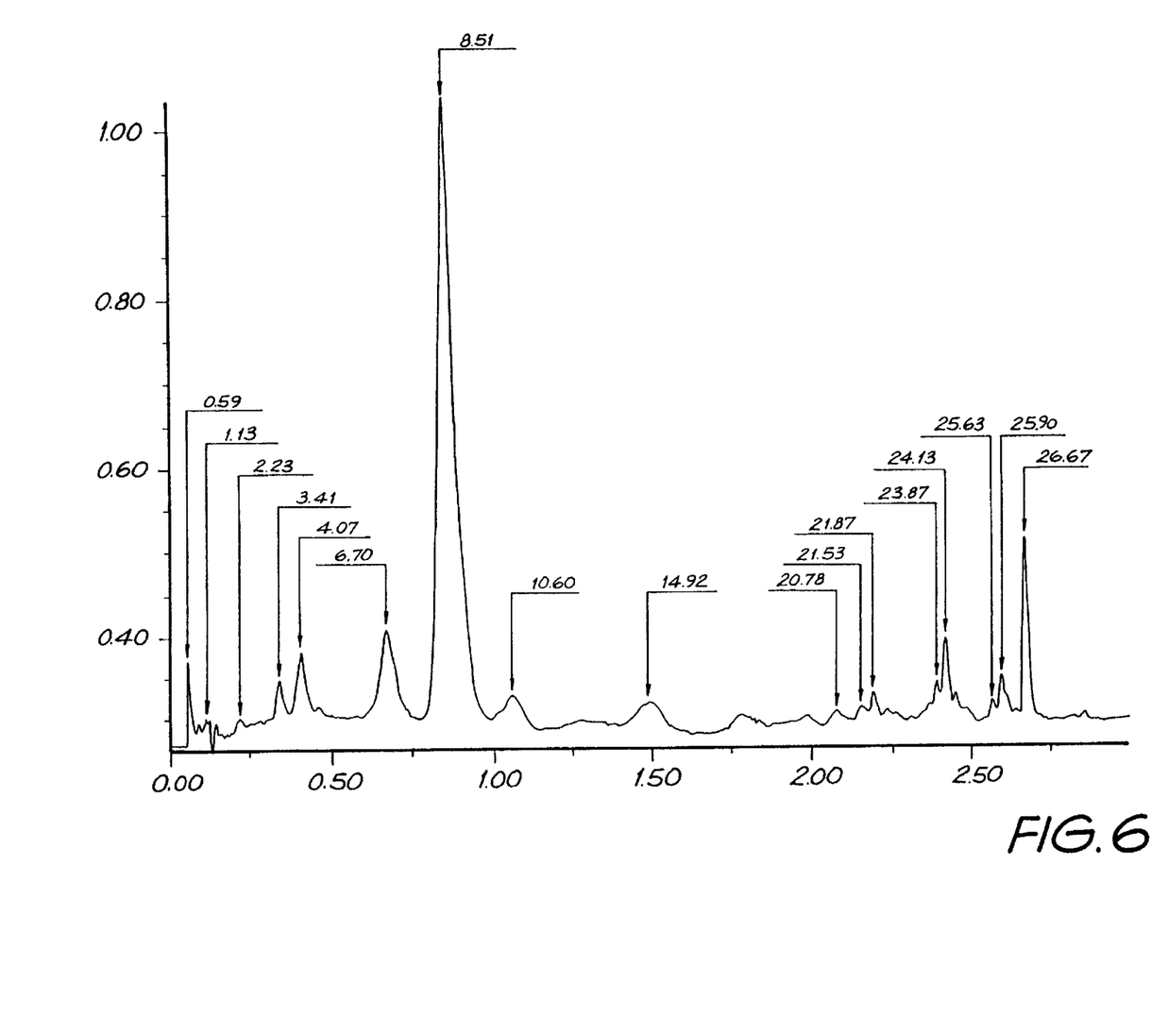
FIG. 6 is a chromatogram of the azadirachtini rich powder produced by the process depicted in FIG. 1.

After concentration in the still 24, the aqueous supernatant contains a fine suspension of solid azadirachtin and the other triterpenes and a slight amount of polysaccharides and proteins carried over in the ethyl acetate extraction. To allow the ready formation of an azadirachtin powder. The water suspension is then extracted with ethyl acetate (step 26). The azadirachtin and other triterpenes partition completely into the ethyl acetate layer. The resulting aqueous layer is slightly discoloured by the slight amount of polysaccharides and proteins and can go to waste. The ethyl acetate in the organic layer is then evaporated in a scrape side rotary evaporator 27 leaving an azadirachtin rich powder 28. The chromatogram, attached as FIG. 6. confirms that the powder is rich in azadirachtin. With the azadirachtini content of the powder being about 48%. The evaporated ethyl acetate 29 can be condensed. Combined with the reclaimed ethyl acetate 19, and re-used in the initial extraction of the expeller cake 14.

Alternative drying techniques including microwave drying of the supernatant can also be readily envisaged.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A process for the production of an azadirachtin rich aqueous solution including the steps of:
   (i) de-oiling by pressing whole neem seeds or ground or otherwise comminuted neem seeds to remove a first proportion of the oil content thereof;
   (ii) extracting the de-oiled neem seeds with a polar organic solvent in which azadirachtin is soluble but in which polysaccharides and proteins are not substantially soluble to form an organic solution of azadirachtin and the remaining oil;
   (iii) partitioning the organic solution against water to form an aqueous solution of azadirachtin and the remaining oil; and
   (iv) separating the remaining oil from the aqueous solution to form an azadirachtin rich aqueous solution and a bitter oil fraction.

2. A process for the production of an azadirachtin rich powder comprising the process as claimed in claim 1 which further includes the steps of:
   (v) extracting the aqueous solution with a polar organic solvent in which polysaccharides and proteins are not substantially soluble, to form an organic solution of azadirachtin; and
   (vi) evaporating the organic solvent to form an azadirachtin rich powder.

3. A process for the production of an azadirachtin rich aqueous solution as claimed in claim 1, in which the neem seeds are first dried to a moisture content of from 1 to 10% by weight and then pressed to produce an expeller cake of seeds from which has been removed a substantial proportion of the oil content of the seeds.

4. A process for the production of an azadirachtin rich aqueous solution as claimed in claim 1, in which the pressing is conducted so that at least 70% to 90% by weight of the oil is removed from the seeds during the pressing process.

5. A process for the production of an azadirachtin rich aqueous solution as claimed in claim 1, in which the polar organic solvent used to extract the substantially de-oiled expeller cake in step (ii) is selected from the group consisting of ethyl acetate, methyl acrylate, butanol, 2-butanone, butyl carbitol, ethylene glycol mono butyl ether, ethyl formate, propyl formate, furan, tetrahydrofuran, isopherone, 2,4-dihydroxy 4-methyl pentanone, 2,4-dimethyl pentanone, dibutyl phthalate, dipentyl phthalate, 1,2-epoxy propane, dibutyl sebacate, chloroform, dimethyl sulphide, ethanthiol, ethyl chloride, pentachloroethane, trichloroethene, 1-bromopentane or mixtures thereof.

6. A process for the production of an azadirachtin rich aqueous solution as claimed in claim 5, in which the polar organic solvent used to extract the substantially de-oiled expeller cake in step (ii) is ethyl acetate.

7. A process for the production of an azadirachtin rich aqueous solution as claimed in claim 1, in which the polar organic solvent used to extract the substantially de-oiled expeller cake in step (ii) is concentrated by distillation under vacuum prior to step (iii).

8. A process for the production of an azadirachtin rich aqueous solution as claimed in claim 7, in which the polar organic solvent used to extract the substantially de-oiled expeller cake in step (ii) is concentrated by distillation under vacuum prior to step (iii) by an amount of up to 50%.

9. A process for the production of an azadirachtin rich aqueous solution as claimed in claim 1 in which the water used in step (iii) has a temperature between 20° C. and 40° C.

10. A process for the production of an azadirachtin rich aqueous solution as claimed in claim 1 in which the aqueous solution formed by the partition with the water is cooled prior to the oil separation step (step (iv)).

11. A process for the production of an azadirachtin rich aqueous solution as claimed in claim 1, in which the separation is undertaken by passing the aqueous solution through a separator where the solution is spun through a series of cones that physically separate the oil and water on the basis of their densities.

12. A process for the production of an azadirachtin rich powder as claimed in claim 2, in which, in step (v), the azadirachtin-rich aqueous solution is extracted with a solvent selected from the group consisting of methyl acrylate butanol, 2-butanone, butyl carbitol, ethylene glycol mono butyl ether, ethyl formate, propel formate, furan, tetrahydrofuran, isopherone, 2,4-dihydroxy 4-methyl pentanone, 2,4-dimethyl pentanone, dibutyl phthalate, dipentyl phthalate, 1,2-epoxy propane, dibutyl sebacate, chloroform, toluene, benzene, dimethyl sulphide, ethanthiol, ethyl chloride, pentachloroethane, trichloroethene, 1-bromopentane or mixtures thereof.

13. A process for the production of an azadirachtin rich powder as claimed in claim 12, in which, in step (v), the azadirachtin-rich aqeous solution is extracted with ethyl acetate.

14. A process for the production of an azadirachtin-rich powder as claimed in claim 12, in which the aqueous solution prior to step (v) is salted to ensure that substantially all of the azadirachtin is removed from the aqueous phase in this step.

15. A process for the production of an azadirachtin rich powder as claimed in claim 2, in which the temperature of the aqueous solution prior to step (v) is lowered to reduce the solubility of the azadirachtin in the aqueous solution.

16. A process for the production of an azadirachtin rich powder as claimed in claim 15, in which the temperature of the aqueous solution is lowered to 10° C. or less.

17. A process for the production of an azadirachtin rich powder as claimed in claim 2, wherein step (vi) includes microwave drying.

18. A process for the production of an azadirachtin rich powder as claimed in claim 2, in which the evaporated ethyl acetate from step (vi) which has not been contaminated with other organic solvents during the process is condensed and recycled ready for immediate use in step (ii) of the extraction process.

19. A process for the production of an azadirachtin rich powder as claimed in claim 2 in which the process includes as an additional step of redissolving the azadirachtin powder in methanol which is then evaporated to produce an even less oily azadirachtin rich powder.

20. A process for the production of an azadirachtin rich powder as claimed in claim 2 in which the process includes a filtering step prior to step (vi).

21. A process for the production of azadirachtin rich powder as claimed in claim 20, in which the filtering step comprises passing the azadirachtin rich supernatant through a hydrophobic filter medium.

22. A process for the production of an azadirachtin rich aqueous solution as claimed in claim 1, in which the neem seeds are first dried to a moisture content of from 2 to 4% by weight, and then pressed to produce an expeller cake from which has been removed a substantial portion of the oil content of the seeds.

23. A process for the production of an azadirachtin rich aqueous solution as claimed in claim 1, in which the pressing is conducted so that at least 70 to 80% by weight of the oil is removed from the seeds during the pressing process.

24. A process for the production of an azadirachtin rich aqueous solution comprising the steps of:

(a) partitioning an organic solution of azadirachtin against water to form an aqueous solution of azadirachtin, the organic solution being formed by the extraction of substantially de-oiled neem seeds with a polar organic solvent in which azadirachtin is soluble but in which polysaccharides and proteins are not substantially soluble; and (b) separating any remaining oil from the aqueous solution to form the azadirachtin rich aqueous solution.

* * * * *

UNITED STATES PATENT AND TRADEMARK OFFICE
CERTIFICATE OF CORRECTION

PATENT NO.    : 6,312,738 B1
DATED         : November 6, 2001
INVENTOR(S)   : O'Shea et al.

It is certified that error appears in the above-identified patent and that said Letters Patent is hereby corrected as shown below:

Column 1,
Line 12, please change "tetraniortriterpenoid" to -- tetranortriterpenoid --.
Line 14, please change "neniatodes" to -- nematodes --.
Line 17, please change "azadirachtini" to -- azadirachtin --.

Column 2,
Line 23, please change "nioni-polar" to -- non-polar --.
Line 23, please change "hexanie" to -- hexane --.

Column 3,
Line 23, please change "azadirachtini" to -- azadirachtin --.
Line 48, please change "azadirachtin. Most of any other highly polar triterpenies" to -- azadirachtin and most of any other highly polar triterpenies --.

Column 6,
Line 11, please change "azadirachtini" to -- azadirachtin --.

Signed and Sealed this

Eleventh Day of March, 2003

JAMES E. ROGAN
*Director of the United States Patent and Trademark Office*